United States Patent [19]

Cesa et al.

[11] Patent Number: 4,740,611
[45] Date of Patent: Apr. 26, 1988

[54] N,N'-DISUBSTITUTED UREAS

[75] Inventors: Mark C. Cesa, South Euclid; James E. Rinz, University Heights; Gilles Klopman, East Cleveland; Teodora T. Kopp, Garfield Hts., all of Ohio

[73] Assignee: The Standard Oil Company, Cleveland, Ohio

[21] Appl. No.: 924,717

[22] Filed: Oct. 30, 1986

[51] Int. Cl.$^4$ .......................... C07C 127/19
[52] U.S. Cl. ........................ 560/34; 560/16; 558/254; 548/335; 548/341; 548/506; 548/507
[58] Field of Search ............... 560/34, 16, 17; 558/254; 548/510, 341, 343, 335, 506, 507; 562/439

[56] References Cited

U.S. PATENT DOCUMENTS 3,808,262  4/1974  Zeeh et al. .................. 560/34

FOREIGN PATENT DOCUMENTS 623988  7/1981  Switzerland .................. 560/34

Primary Examiner—Michael L. Shippen
Assistant Examiner—Bruce D. Gray
Attorney, Agent, or Firm—Charles S. Lynch; Vincent E. Young; Larry W. Evans

[57] ABSTRACT

Disclosed are new compounds

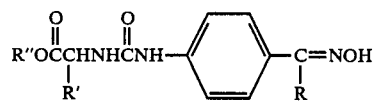

where each of R and R' have zero to 10 C atoms; R is H or hydrocarbyl; R' is H, hydrocarbyl, or hydrocarbyl substituted with hydrocarbylcarbonylamino, di(hydrocarbylcarbonyl)amino, hydrocarbylcarbonyl(hydrocarbyl)amino, formylamino, diformylamino and formyl(hydrocarbyl)amino, hydrocarbyloxy, hydrocarbylthio, formylthio, hydrocarbylcarbonylthio, hydrocarbyloxycarbonyl, hydrocarbyl carboxyl, hydrocarbylamino, dihydrocarbylamino, formyl, 3-indolyl, 3-(1-hydrocarbyl)indolyl, 3-(1-hydrocarbylcarbonyl)indolyl, 3-(1-formyl)indolyl, carbamoyl, hydrocarbylcarbamoyl, dihydrocarbylcarbamoyl, 5-imidazolyl, 5-(3-hydrocarbyl)imidazolyl, 5-(3-hydrocarbylcarbonyl)imidazolyl, or 5-(3-formyl)imidazolyl, and R" is phenyl or a $C_1$ to $C_6$ alkyl group; and methods of making such compounds.

7 Claims, No Drawings

N,N'-DISUBSTITUTED UREAS

This invention relates to new compounds of the formula,

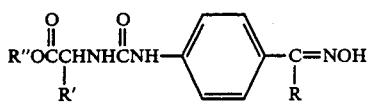

Formula (1)

where each of R and R' has zero to 10 C atoms and no ethylenic or acetylenic unsaturation; R is H or hydrocarbyl; R' is H, hydrocarbyl, or hydrocarbyl substituted with hydrocarbylcarbonylamino, di(hydrocarbylcarbonyl)amino, hydrocarbylcarbonyl(hydrocarbyl)amino, formylamino, diformylamino; and formyl(hydrocarbyl)amino, hydrocarbyloxy, hydrocarbylthio, formylthio, hydrocarbylcarbonylthio, hydrocarbyloxycarbonyl, hydrocarbyl carboxyl, hydrocarbylamino, dihydrocarbylamino, formyl, 3-indolyl, 3-(1-hydrocarbyl)indolyl, 3-(1-hydrocarbylcarbonyl)indolyl, 3-(1-formyl)indolyl, carbamoyl, hydrocarbylcarbamoyl, dihydrocarbylcarbamoyl, 5-imidazolyl, 5-(3-hydrocarbyl)imidazolyl, 5-(3-hydrocarbylcarbonyl)imidazolyl, or 5-(3-formyl)imidazolyl, and R" is phenyl or a $C_1$ to $C_6$ alkyl group. Usually R contains 0 to 6 C atoms.

These compounds are useful ultraviolet light absorbers. They can be used in plastic compositions to impart this property. It is believed that the excellent UV light absorption of these compounds is related to the fact that the compounds of the invention have the oxime, arene and urea chromophores in conjugation. Such structures are believed to be novel.

The compounds of the invention all have high molar extinction coefficients, $\lambda_{max}$=250–290 nm, $\epsilon \geq 10^4$. In our work the particular solvent used in measuring the absorbance to determine the extinction coefficients was methanol.

The products of the present invention where R is H can be prepared by reacting the compound

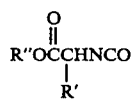

Formula (2)

with an acetal of 4-aminobenzaldehyde derived from a $C_1$ to $C_6$ monoalkanol or a $C_1$ to $C_6$ alkanediol, said reaction being carried out in a solvent such as dioxane, THF, diethyl ether, glymes and di-n-butyl ether in the presence of pyridine, and then reacting the product of such reaction with hydroxylamine hydrochloride in methanol as the solvent to obtain the compound of formula (1) where R is H.

The products of the present invention where R is hydrocarbyl can be made conveniently by reacting the compound of formula (2) with

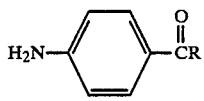

in one of the same solvents (dioxane, THF, etc.) to obtain the compound,

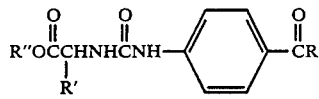

Formula (3)

which is then separated from the solvent. This product is reacted in methanol solvent with hydroxylamine hydrochloride to obtain the compound of formula (1).

The starting material isocyanate for either reaction scheme can be made by reacting the compound

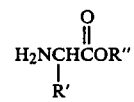

Formula (4)

or its hydrochloride with diphosgene in the manner illustrated in the examples herein. In the reaction scheme first described, the starting material acetal for reacting with the isocyanate can conveniently be made by first making the acetal of 4-nitrobenzaldehyde and then hydrogenating such acetal over platinum oxide catalyst to make the corresponding 4-aminobenzaldehyde acetal, all as illustrated in specific examples.

In addition to the new compounds of the invention, we have discovered a new and unobvious process for making the compound

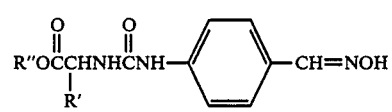

Formula (5)

where R' contains no ethylenic or acetylenic unsaturation, R' has zero to 10 C atoms and is H, hydrocarbyl or hydrocarbyl substituted with hydrocarbylcarbonylamino, di(hydrocarbylcarbonyl)amino, hydrocarbylcarbonyl(hydrocarbyl)amino, formylamino, diformylamino; formyl(hydrocarbyl)amino, hydrocarbyloxy, hydrocarbylthio, formylthio, hydrocarbylcarbonylthio, hydrocarbyloxycarbonyl, hydrocarbyl carboxyl, hydrocarbylamino, dihydrocarbylamino, formyl, 3-indolyl, 3-(1-hydrocarbyl)indolyl, 3-(1-hydrocarbylcarbonyl)indolyl, 3-(1-formyl)indolyl, carbamoyl, hydrocarbylcarbamoyl, dihydrocarbylcarbamoyl, 5-imidazolyl, 5-(3-hydrocarbyl)imidazolyl, 5-(3-hydrocarbylcarbonyl)imidazolyl, or 5-(3-formyl)imidazolyl, and R" is phenyl or a $C_1$ or $C_6$ alkyl group, which comprises reacting a compound,

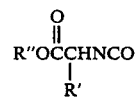

with an acetal of 4-aminobenzaldehyde derived from a $C_1$ to $C_6$ monoalkanol or a $C_1$ to $C_6$ alkanediol and in the presence of pyridine, and then reacting the product of such reaction with hydroxylamine hydrochloride in an alcohol solvent. In the process, the reaction mixture is kept substantially free of water so as not to hydrolyze the isocyanate group. A small amount of water can be tolerated, say 0.2 moles per mole of starting material isocyanate, and such amount as is present represents a likely loss of the isocyanate.

The reaction is unobvious in that removal of the acetal function occurs during the course of the coupling and oximation reactions, and need not be carried out as a separate step.

Two examples of the usefulness of the present compounds are as follows:

BLOW MOLDED LDPE BOTTLES 1 part substituted urea compound is blended with 1000 parts low-density polyethylene in a plasticating screw extruder, pelletized, and blow molded to give a bottle which has substantially reduced UV transparency compared with a bottle made without the urea compound.

POLYETHYLENE SHEET 1 part substituted urea compound is blended with 1000 parts low-density polyethylene in a plasticating screw extruder and then extrusion blow molded into 6 mil film which exhibits substantially reduced UV transparency compared with film not containing the urea compound.

The following examples are merely illustrative and are not to be considered as limiting.

EXAMPLE 1

4-Nitrobenzaldehyde ethylene glycol acetal is made as follows: A mixture of 75.5 g 4-nitrobenzaldehyde, 100 mL ethylene glycol, and 2.5 g 4-toluenesulfonic acid in 500 mL toluene is heated with stirring to reflux under $N_2$ for 5 hours in a 1000 mL round bottom flask equipped with a Dean-Stark trap and reflux condenser. During this time about 20 mL of a mixture of water and ethylene glycol is collected in the trap. The product mixture is washed with two 100 mL portions of saturated aqueous sodium bicarbonate solution and with 100 mL water. The organic layer is dried over $MgSO_4$, and the solvent is distilled off on rotary evaporator. The resultant yellow solid is recrystallized from ethanol to give a yellow crystalline solid, mp. 87°–88° C., yield = 80–85%.

A mixture of 19.5 g of the 4-nitrobenzaldehyde ethylene glycol acetal, 21.2 g trimethyl orthoformate, and 2 g $PtO_2$ in 250 mL anhydrous THF is placed in a 450 mL Parr stirred autoclave. The contents are purged with $N_2$, with the contents kept between 7° and 10° C. by external cooling. 100 psig $H_2$ is pressed in, and the reaction mixture is stirred. The reaction mixture warms to 20° C., and external cooling (ice bath) is maintained. The $H_2$ pressure is maintained at 100 psi by repressurization several times over a 14–18 minute period. The temperature then begins to drop, and little further drop in $H_2$ is noted. The reaction mixture is stirred for a total of 45 minutes, after which time the reaction temperature returns to 7°–10° C. The autoclave is vented and opened, and the pale yellow product solution is filtered, dried over $CaSO_4$, refiltered, and distilled to dryness by rotary evaporator. The product 4-aminobenzaldehyde ethylene glycol acetal, a nearly white solid, is collected in over 90% yield (mp.=71°–73° C.)

DL-alanine methyl ester isocyanate is made as follows: 38.8 mL diphosgene is added dropwise over 1 hour to a mixture of 38.92 g DL-alanine methyl ester hydrochloride and 0.4 g activated charcoal in 400 mL dioxane under $N_2$. The reaction mixture is warmed to 75°–80° C. during this time. The reaction mixture is then heated and stirred at reflux for 2½ hours. The reaction mixture is then cooled, filtered, and concentrated to dryness by rotary evaporator, keeping exposure to moisture to a minimum. The crude product is re-dissolved in 100 mL THF, and the pH of the solution is adjusted to 5.5–6.0 by addition of pyridine. The product mixture is again filtered, and the filtrate is fractionally distilled to give pure DL-alanine methyl ester isocyanate in about 60% yield (b.p. 70° C., 10 mm Hg.).

N-[4-(hydroxyiminomethyl)phenyl]-N'-(1-methoxycarbonylethyl)urea is prepared as follows: A solution of 0.1 mol of 4-aminobenzaldehyde ethylene glycol acetal in 100 mL of anhydrous THF is added dropwise over 10 minutes to a solution of 0.1 mol DL-alanine methyl ester isocyanate and 0.35 mol pyridine in 100 mL THF at room temperature under $N_2$. The yellow reaction mixture is stirred at room temperature for 2 hours. After ½ hour a yellow-orange precipitate begins to form. After 2 hours the solvent is removed by rotary evaporator to give an orange, semisolid mass. A solution of 0.11 mol hydroxylamine hydrochloride and 0.1 mol trimethyl orthoformate in $CH_3OH$ is added, and the reaction mixture is heated to reflux under $N_2$ for 1 hour. The reaction mixture is reduced to about ¼ volume by rotary evaporator, and water is added. Off-white crystals of product form after 2 hours of stirring. The crystals are isolated by filtration and dried overnight in a vacuum oven at 50°–55° C. The yield of product (mp 143°–145.5° C.) is about 60%.

EXAMPLE 2

38.8 mL diphosgene is added dropwise over 1 hour to a mixture of 35 g glycine methyl ester hydrochloride and 0.4 g activated charcoal in 400 mL dioxane under $N_2$. The reaction mixture is warmed to 80° C. during this time. The reaction mixture is then heated and stirred at reflux for 2½ hours. The reaction mixture is then cooled, filtered, and concentrated to dryness by rotary evaporator, keeping exposure to moisture to a minimum. The crude product is re-dissolved in 100 mL THF, and the pH of the solution is adjusted to 5.5–6.0 by addition of pyridine. The product mixture is again filtered, and the filtrate is fractionally distilled to give pure glycine methyl ester isocyanate in about 70% yield (b.p. 60° C., 13 mm Hg.).

A solution of 0.1 mol of 4-aminobenzaldehyde ethylene glycol acetal in 100 mL of anhydrous THF is added dropwise over 10 minutes to a solution of 0.1 mol of glycine methyl ester isocyanate and 0.35 mol pyridine in 100 mL THF at room temperature under $N_2$. The yellow reaction mixture is stirred at room temperature for 2 hours. After ¼ hour a yellow-orange precipitate begins to form. After 2 hours the solvent is removed by rotary evaporator to give an orange semisolid mass. A solution of 0.11 mol hydroxylamine hydrochloride and 0.1 mol trimethyl orthoformate in $CH_3OH$ is added, and the reaction mixture is heated to reflux under $N_2$ for 1 hour. The reaction mixture is reduced to about ¼ volume by rotary evaporator, and water is added. Pale yellow crystals of N-[4-(hydroxyiminomethyl)phenyl]-N'-methoxycarbonylmethylurea form after ½ hour. The product crystals are isolated by filtration and dried overnight in a vacuum at 50°–55° C. The yield of crude product (mp 158°–161° C.): 70–75%.

The product is purified by recrystallization from a 10:6:1 solution of $CH_3OH:H_2O$: compound. The product is washed with cold water and dried in a vacuum oven at 50° C. to give off-white crystals, mp. 167.5°–168.5° C. Elemental analysis: calcd. C 52.59, H 5.22, N 16.72; found C 52.38, H 5.16, N 16.65. $^1H$ NMR (acetone-d$_6$): δ10.15s, 1H, —NO$\underline{H}$; 8.4s, 1H, —N$\underline{H}$—; 8.1s/d, 1H, —C$\underline{H}$=N; 7.55bs, 4$\underline{H}$, phenyl; 6.21s/d, 1H, —N$\underline{H}$—; 4.02s/d, 2H, —C$\underline{H}_2$—; 3.74s, 3H, C$\underline{H}_3$O—. $^{13}$C NMR (acetone-d$_6$): δ172, —$\underline{C}$OO—; 156, —N-$\underline{C}$ON—; 149, —$\underline{C}$H=N—; 119, 128, 142, phenyl; 52, $\underline{C}$H$_3$O—; 42, —$\underline{C}$H$_2$—. UV-vis (CH$_3$OH): λ$_{max}$=279 nm, ε=2.90×10$^4$.

EXAMPLE 3

9.7 mL diphosgene is added dropwise over 50 minutes to a mixture of 12.85 g dimethyl aminomalonate hydrochloride and 0.1 g activated charcoal in 25 mL dioxane under N$_2$. The reaction mixture is warmed to 75°–80° C. during this time. The reaction mixture is then heated and stirred at reflux for 2½ hours. The reaction mixture is then cooled, filtered, and concentrated to dryness by rotary evaporator, keeping exposure to moisture to a minimum. The crude product is purified by fractional distillation (bp 80°–85° C., <1 mm Hg) to give pure dimethyl isocyanatomalonate in >80% yield.

N-[4-(hydroxyiminomethyl)phenyl]-N'-bis(methoxycarbonyl)methylurea is made as follows: A solution of 0.1 mol of 4-aminobenzaldehyde ethylene glycol acetal in 100 mL of anhydrous THF is added dropwise over 10 minutes to a solution of 0.1 mol of the dimethyl aminomalonate isocyanate and 0.35 mol pyridine in 100 mL THF at room temperature under N$_2$. The yellow reaction mixture is stirred at room temperature for 2 hours. After ½ hour a precipitate begins to form. After 2 hours the solvent is removed by rotary evaporator to give a yellow, semisolid mass. A solution of 0.11 mol hydroxylamine hydrochloride and 0.1 mol trimethyl orthoformate in CH$_3$OH is added, and the reaction mixture is heated to reflux under N$_2$ for 1 hour. The reaction mixture is reduced to about ¼ volume by rotary evaporator, and water is added. Off-white crystals of product form, which are isolated by filtration and dried overnight in a vacuum oven at 50°–55° C. The yield of crude product (mp 164°–166° C.): 75–80%.

The product is purified by multiple extraction with ethanol until the washings are no longer yellow. White crystals result, m.p. 161.5°–162.5° C. Elemental analysis: calcd. C 50.49, N 4.89, N 13.59; found C 50.88, H 4.90, N 13.52. $^1$H NMR (acetone-d$_6$-DMSO-d$_6$): δ10.95 s, 1H, —NO$\underline{H}$; 9.1s, 1H, —N$\underline{H}$—; 8.1s, 1H, —C$\underline{H}$=N—; 7.55bs, 4$\underline{H}$, phenyl; 7.15d, 1H, —N$\underline{H}$—; 5.15s/d, 1H, —C$\underline{H}$—; 3.80s, 3H, C$\underline{H}_3$O—. $^{13}$C NMR (acetone-d$_6$-DMSO-d$_6$): δ168, —$\underline{C}$OO—; 155, —N$\underline{C}$ON—; 148, —$\underline{C}$H=N—; 118, 128, 142, phenyl; 58, —$\underline{C}$H$_2$—; 53, $\underline{C}$H$_3$O—. UV-vis (CH$_3$OH): λ$_{max}$=276 nm, ε=3.06×10$^4$.

EXAMPLE 4

0.35 mol diphosgene is added dropwise over 1 hour to a mixture of 0.28 mol of the dimethyl ester of aspartic acid and 0.4 g activated charcoal in 400 mL dioxane under N$_2$. The reaction mixture is warmed to 75°–80° C. during this time. The reaction mixture is then heated and stirred at reflux for 2½ hours. The reaction mixture is then cooled, filtered, and concentrated to dryness by rotary evaporator, keeping exposure to moisture to a minimum. The crude product is re-dissolved in 100 mL THF, and the pH of the solution is adjusted to 5.5–6.0 by addition of pyridine. The product mixture is again filtered, and the filtrate is fractionally distilled to give dimethyl aspartate isocyanate.

A solution of 0.1 mol of 4-aminobenzaldehyde ethylene glycol acetal in 100 mL of anhydrous THF is added dropwise over 10 minutes to a solution of 0.1 mol of dimethyl aspartate isocyanate and 0.35 mol pyridine in 100 mL THF at room temperature under N$_2$. The reaction mixture is stirred at room temperature for 2 hours. After 2 hours the solvent is removed by rotary evaporator. A solution of 0.11 mol hydroxylamine hydrochloride and 0.1 mol trimethyl orthoformate in CH$_3$OH is added, and the reaction mixture is heated to reflux under N$_2$ for 1 hour. The reaction mixture is reduced to about ¼ volume by rotary evaporator, and water is added. N-[4-(hydroxyiminomethyl)phenyl]-N'-1-[1,2-bis(methoxycarbonyl)ethyl]urea forms after several hours of stirring. The product is isolated by filtration and dried overnight in a vacuum oven at 50°–55° C.

EXAMPLE 5

0.35 mol diphosgene is added dropwise over 1 hour to a mixture of 0.28 mol of the dimethyl ester of glutamic acid and 0.4 g activated charcoal in 400 mL dioxane under N$_2$. The reaction mixture is then heated and stirred at reflux for 2½ hours. The reaction mixture is then cooled, filtered, and concentrated to dryness by rotary evaporator, keeping exposure to moisture to a minimum. The crude product is re-dissolved in 100 mL THF, and the pH of the solution is adjusted to 5.5–6.0 by addition of pyridine. The product mixture is again filtered, and the filtrate is fractionally distilled to give dimethyl glutamate isocyanate.

A solution of 0.1 mol of 4-aminobenzaldehyde ethylene glycol acetal in 100 mL of anhydrous THF is added dropwise over 10 minutes to a solution of 0.1 mol of dimethyl glutamate isocyanate and 0.35 mol pyridine in 100 mL THF at room temperature under N$_2$. The reaction mixture is stirred at room temperature for 2 hours. After 2 hours the solvent is removed by rotary evaporator. A solution of 0.11 mol hydroxylamine hydrochloride and 0.1 mol trimethyl orthoformate in CH$_3$OH is added, and the reaction mixture is heated to reflux under N$_2$ for 1 hour. The reaction mixture is reduced to about ¼ volume by rotary evaporator, and water is added. N-[4-(hydroxyiminomethyl)phenyl]-N'-1-[1,3-bis(methoxycarbonyl)propyl]urea forms after several hours of stirring. The product is isolated by filtration and dried overnight in a vacuum oven at 50°–55° C.

EXAMPLE 6

0.35 mol diphosgene is added dropwise over 1 hour to a mixture of 0.28 mol of the methyl ester of valine and 0.4 g activated charcoal in 400 mL dioxane under N$_2$. The reaction mixture is then heated and stirred at reflux for 2½ hours. The reaction mixture is then cooled, filtered, and concentrated to dryness by rotary evaporator, keeping exposure to moisture to a minimum. The crude product is re-dissolved in 100 mL THF, and the pH of the solution is adjusted to 5.5–6.0 by addition of pyridine. The product mixture is again filtered, and the filtrate is fractionally distilled to give valine methyl ester isocyanate.

A solution of 0.1 mol of 4-aminobenzaldehyde ethylene glycol acetal in 100 mL of anhydrous THF is added dropwise over 10 minutes to a solution of 0.1 mol of valine methyl ester isocyanate and 0.35 mol pyridine in 100 mL THF at room temperature under N$_2$. The reaction mixture is stirred at room temperature for 2 hours. After 2 hours the solvent is removed by rotary evaporator. A solution of 0.11 mol hydroxylamine hydrochloride and 0.1 mol trimethyl orthoformate in CH$_3$OH is added, and the reaction mixture is heated to reflux under N₂ for 1 hour. The reaction mixture is reduced to about ¼ volume by rotary evaporator, and water is added. N-[4-hydroxyiminomethyl)phenyl]-N'-[1-(1-methoxycarbonyl-2-methyl)propyl]urea forms after several hours of stirring. The product is isolated by filtration and dried overnight in a vacuum oven at 50°–55° C.

EXAMPLE 7

A solution of 0.1 mol of 4-aminobenzaldehyde ethylene glycol acetal in 100 mL of anhydrous THF is added dropwise over 10 minutes to a solution of 0.1 mol of glycine ethyl ester isocyanate and 0.35 mol pyridine in 100 mL THF at room temperature under N₂. The reaction mixture is stirred at room temperature for 2 hours. After 2 hours the solvent is removed by rotary evaporator. A solution of 0.11 mol hydroxylamine hydrochloride and 0.1 mol trimethyl orthoformate in CH₃OH is added, and the reaction mixture is heated to reflux under N₂ for 1 hour. The reaction mixture is reduced to about ¼ volume by rotary evaporator, and water is added. N-[4-(hydroxyiminomethyl)phenyl]-N'-ethoxycarbonylmethylurea forms after several hours of stirring. The product is isolated by filtration and dried overnight in a vacuum at 50°–55° C.

EXAMPLE 8

A solution of 0.1 mol of 4-aminobenzaldehyde ethylene glycol acetal in 100 mL of anhydrous THF is added dropwise over 10 minutes to a solution of 0.1 mol of glycine n-propyl ester isocyanate and 0.35 mol pyridine in 100 mL THF at room temperature under N₂. The reaction mixture is stirred at room temperature for 2 hours. After 2 hours the solvent is removed by rotary evaporator. A solution of 0.11 mol hydroxylamine hydrochloride and 0.1 mol trimethyl orthoformate in CH₃OH is added, and the reaction mixture is heated to reflux under N₂ for 1 hour. The reaction mixture is reduced to about ¼ volume by rotary evaporator, and water is added. N-[4-(hydroxyiminomethyl)phenyl]-N'-(n-propoxycarbonylmethyl)urea forms after several hours of stirring. The product is isolated by filtration and dried overnight in a vacuum at 50°–55° C.

EXAMPLE 9

A solution of 0.1 mol of 4-aminobenzaldehyde ethylene glycol acetal in 100 mL of anhydrous THF is added dropwise over 10 minutes to a solution of 0.1 mol of glycine isopropyl ester isocyanate and 0.35 mol pyridine in 100 mL THF at room temperature under N₂. The reaction mixture is stirred at room temperature for 2 hours. After 2 hours the solvent is removed by rotary evaporator. A solution of 0.11 mol hydroxylamine hydrochloride and 0.1 mol trimethyl orthoformate in CH₃OH is added, and the reaction mixture is heated to reflux under N₂ for 1 hour. The reaction mixture is reduced to about ¼ volume by rotary evaporator, and water is added. N-[4-(hydroxyiminomethyl)phenyl]-N'-isopropoxycarbonylmethylurea forms after 2 hours of stirring. The product is isolated by filtration and dried overnight in a vacuum at 50°–55° C.

EXAMPLE 10

A solution of 0.1 mol of 4-aminobenzaldehyde ethylene glycol acetal in 100 mL of anhydrous THF is added dropwise over 10 minutes to a solution of 0.1 mol of glycine t-butyl ester isocyanate and 0.35 mol pyridine in 100 mL THF at room temperature under N₂. The reaction mixture is stirred at room temperature for 2 hours. After 2 hours the solvent is removed by rotary evaporator. A solution of 0.11 mol hydroxylamine hydrochloride and 0.1 mol trimethyl orthoformate in CH₃OH is added, and the reaction mixture is heated to reflux under N₂ for 1 hour. The reaction mixture is reduced to about ¼ volume by rotary evaporator, and water is added. N-[4-(hydroxyiminomethyl)phenyl]-N'-(t-butoxycarbonylmethyl)urea forms after several hours of stirring. The product is isolated by filtration and dried overnight in a vacuum at 50°–55° C.

EXAMPLE 11

A solution of 0.1 mol of 4-aminobenzaldehyde ethylene glycol acetal in 100 mL of anhydrous THF is added dropwise over 10 minutes to a solution of 0.1 mol of glycine phenyl ester isocyanate and 0.35 mol pyridine in 100 mL THF at room temperature under N₂. The reaction mixture is stirred at room temperature for 2 hours. After 2 hours the solvent is removed by rotary evaporator. A solution of 0.11 mol hydroxylamine hydrochloride and 0.1 mol trimethyl orthoformate in CH₃OH is added, and the reaction mixture is heated to reflux under N₂ for 1 hour. The reaction mixture is reduced to about ¼ volume by rotary evaporator, and water is added. N-[4-(hydroxyiminomethyl)phenyl]-N'-phenoxycarbonylmethylurea forms after several hours of stirring. The product is isolated by filtration and dried overnight in a vacuum at 50°–55° C.

EXAMPLE 12

0.35 mol diphosgene is added dropwise over 1 hour to a mixture of 0.28 mol of the methyl ester of leucine and 0.4 g activated charcoal in 400 mL dioxane under N₂. The reaction mixture is then heated and stirred at reflux for 2½ hours. The reaction mixture is then cooled, filtered, and concentrated to dryness by rotary evaporator, keeping exposure to moisture to a minimum. The crude product is re-dissolved in 100 mL THF, and the pH of the solution is adjusted to 5.5–6.0 by addition of pyridine. The product mixture is again filtered, and the filtrate is fractionally distilled to give leucine methyl ester isocyanate.

A solution of 0.1 mol of 4-aminobenzaldehyde ethylene glycol acetal in 100 mL of anhydrous THF is added dropwise over 10 minutes to a solution of 0.1 mol of leucine methyl ester isocyanate and 0.35 mol pyridine in 100 mL THF at room temperature under N₂. The reaction mixture is stirred at room temperature for 2 hours. After 2 hours the solvent is removed by rotary evaporator. A solution of 0.11 mol hydroxylamine hydrochloride and 0.1 mol trimethyl orthoformate in CH₃OH is added, and the reaction mixture is heated to reflux under N₂ for 1 hour. The reaction mixture is reduced to about ¼ volume by rotary evaporator, and water is added. N-[4-(hydroxyiminomethyl)phenyl]-N'-(1-methoxycarbonyl-3-methylbutyl)urea forms after several hours of stirring. The product is isolated by filtration and dried overnight in a vaccum oven at 50°–55° C.

EXAMPLE 13

0.35 mol diphosgene is added dropwise over 1 hour to a mixture of 0.28 mol of the methyl ester of isoleucine and 0.4 g activated charcoal in 400 mL dioxane under N₂. The reaction mixture is then heated and stirred at reflux for 2½ hours. The reaction mixture is then cooled, filtered, and concentrated to dryness by rotary evaporator, keeping exposure to moisture to a minimum. The crude product is re-dissolved in 100 mL THF, and the pH of the solution is adjusted to 5.5–6.0 by addition of pyridine. The product mixture is again filtered, and the filtrate is fractionally distilled to give isoleucine methyl ester isocyanate.

A solution of 0.1 mol of 4-aminobenzaldehyde ethylene glycol acetal in 100 mL of anhydrous THF is added dropwise over 10 minutes to a solution of 0.1 mol of isoleucine methyl ester isocyanate and 0.35 mol pyridine in 100 mL THF at room temperature under $N_2$. The reaction mixture is stirred at room temperature for 2 hours. After 2 hours the solvent is removed by rotary evaporator. A solution of 0.11 mol hydroxylamine hydrochloride and 0.1 mol trimethyl orthoformate in $CH_3OH$ is added, and the reaction mixture is heated to reflux under $N_2$ for 1 hour. The reaction mixture is reduced to about ¼ volume by rotary evaporator, and water is added. N-[4-(hydroxyiminomethyl)phenyl]-N'-(1-methoxycarbonyl-2-methylbutyl)urea forms after several hours of stirring. The product is isolated by filtration and dried overnight in a vacuum oven at 50°–55° C.

EXAMPLE 14

0.35 mol diphosgene is added dropwise over 1 hour to a mixture of 0.28 mol of the methyl ester of methionine and 0.4 g activated charcoal in 400 mL dioxane under $N_2$. The reaction mixture is then heated and stirred at reflux for 2½ hours. The reaction mixture is then cooled, filtered, and concentrated to dryness by rotary evaporator, keeping exposure to moisture to a minimum. The crude product is re-dissolved in 100 mL THF, and the pH of the solution is adjusted to 5.5–6.0 by addition of pyridine. The product mixture is again filtered, and the filtrate is fractionally distilled to give methionine methyl ester isocyanate.

A solution of 0.1 mol of 4-aminobenzaldehyde ethylene glycol acetal in 100 mL of anhydrous THF is added dropwise over 10 minutes to a solution of 0.1 mol of methionine methyl ester isocyanate and 0.35 mol pyridine in 100 mL THF at room temperature under $N_2$. The reaction mixture is stirred at room temperature for 2 hours. After 2 hours the solvent is removed by rotary evaporator. A solution of 0.11 mol hydroxylamine hydrochloride and 0.1 mol trimethyl orthoformate in $CH_3OH$ is added, and the reaction mixture is heated to reflux under $N_2$ for 1 hour. The reaction mixture is reduced to about ¼ volume by rotary evaporator, and water is added. N-[4-hydroxyiminomethyl)phenyl]-N'-(1-methoxycarbonyl-3-methylthiopropyl)urea forms after several hours of stirring. The product is isolated by filtration and dried overnight in a vacuum oven at 50°–55° C.

EXAMPLE 15

0.35 mol diphosgene is added dropwise over 1 hour to a mixture of 0.28 mol of the methyl ester of phenylalanine and 0.4 g activated charcoal in 400 mL dioxane under $N_2$. The reaction mixture is then heated and stirred at reflux for 2½ hours. The reaction mixture is then cooled, filtered, and concentrated to dryness by rotary evaporator, keeping exposure to moisture to a minimum. The crude product is re-dissolved in 100 mL THF, and the pH of the solution is adjusted to 5.5–6.0 by addition of pyridine. The product mixture is again filtered, and the filtrate is fractionally distilled to give phenylalanine methyl ester isocyanate.

A solution of 0.1 mol of 4-aminobenzaldehyde ethylene glycol acetal in 100 mL of anhydrous THF is added dropwise over 10 minutes to a solution of 0.1 mol of phenylalanine methyl ester isocyanate and 0.35 mol pyridine in 100 mL THF at room temperature under $N_2$. The reaction mixture is stirred at room temperature for 2 hours. After 2 hours the solvent is removed by rotary evaporator. A solution of 0.11 mol hydroxylamine hydrochloride and 0.1 mol trimethyl orthoformate in $CH_3OH$ is added, and the reaction mixture is heated to reflux under $N_2$ for 1 hour. The reaction mixture is reduced to about ¼ volume by rotary evaporator, and water is added. N-[4-(hydroxyiminomethyl)phenyl]-N'-(1-methoxycarbonyl-2-phenylethyl)urea forms after several hours of stirring. The product is isolated by filtration and dried overnight in a vacuum oven at 50°–55° C.

EXAMPLE 16

0.35 mol diphosgene is added dropwise over 1 hour to a mixture of 0.28 mol of the methyl ester of 2-amino-3-(1-acetyl-3-indole)propanoic acid and 0.4 g activated charcoal in 400 mL dioxane under $N_2$. The reaction mixture is then heated and stirred at reflux for 2½ hours. The reaction mixture is then cooled, filtered, and concentrated to dryness by rotary evaporator, keeping exposure to moisture to a minimum. The crude product is re-dissolved in 100 mL THF, and the pH of the solution is adjusted to 5.5–6.0 by addition of pyridine. The product mixture is again filtered, and the filtrate is fractionally distilled to give 2-isocyanato-3-(1-acetyl-3-indole)propanoic acid methyl ester.

A solution of 0.1 mol of 4-aminobenzaldehyde ethylene glycol acetal in 100 mL of anhydrous THF is added dropwise over 10 minutes to a solution of 0.1 mol of 2-isocyanato-3-(1-acetyl-3-indole)propanoic acid methyl ester and 0.35 mol pyridine in 100 mL THF at room temperature under $N_2$. The reaction mixture is stirred at room temperature for 2 hours. After 2 hours the solvent is removed by rotary evaporator. A solution of 0.11 mol hydroxylamine hydrochloride and 0.1 mol trimethyl orthoformate in $CH_3OH$ is added, and the reaction mixture is heated to reflux under $N_2$ for 1 hour. The reaction mixture is reduced to about ¼ volume by rotary evaporator, and water is added. N-[4-(hydroxyiminomethyl)phenyl]-N'-[1-methoxycarbonyl-2-(1-acetyl-3-indolyl)ethyl]urea forms after several hours of stirring. The product is isolated by filtration and dried overnight in a vacuum oven at 50°–55° C.

EXAMPLE 17

0.35 mol diphosgene is added dropwise over 1 hour to a mixture of 0.28 mol of the methyl ester of O-acetylserine and 0.4 g activated charcoal in 400 mL dioxane under $N_2$. The reaction mixture is then heated and stirred at reflux for 2½ hours. The reaction mixture is then cooled, filtered, and concentrated to dryness by rotary evaporator, keeping exposure to moisture to a minimum. The crude product is re-dissolved in 100 mL THF, and the pH of the solution is adjusted to 5.5–6.0 by addition of pyridine. The product mixture is again filtered, and the filtrate is fractionally distilled to give O-acetylserine methyl ester isocyanate.

A solution of 0.1 mol of 4-aminobenzaldehyde ethylene glycol acetal in 100 mL of anhydrous THF is added dropwise over 10 minutes to a solution of 0.1 mol of O-acetylserine methyl ester isocyanate and 0.35 mol pyridine in 100 mL THF at room temperature under N$_2$. The reaction mixture is stirred at room temperature for 2 hours. After 2 hours the solvent is removed by rotary evaporator. A solution of 0.11 mol hydroxylamine hydrochloride and 0.1 mol trimethyl orthoformate in CH$_3$OH is added, and the reaction mixture is heated to reflux under N$_2$ for 1 hour. The reaction mixture is reduced to about ¼ volume by rotary evaporator, and water is added. N-[4-(hydroxyiminomethyl)phenyl]-N'-(1-methoxycarbonyl-2-acetyloxymethyl)urea forms after several hours of stirring. The product is isolated by filtration and dried overnight in a vacuum oven at 50°–55° C.

EXAMPLE 18

0.35 mol disphogene is added dropwise over 1 hour to a mixture of 0.28 mol of the methyl ester of O-acetyl-threonine and 0.4 g activated charcoal in 400 mL dioxane under N$_2$. The reaction mixture is then heated and stirred at reflux for 2½ hours. The reaction mixture is then cooled, filtered, and concentrated to dryness by rotary evaporator, keeping exposure to moisture to a minimum. The crude product is re-dissolved in 100 mL THF, and the pH of the solution is adjusted to 5.5–6.0 by addition of pyridine. The product mixture is again filtered, and the filtrate is fractionally distilled to give O-acetylthreonine methyl ester isocyanate.

A solution of 0.1 mol of 4-aminobenzaldehyde ethylene glycol acetal in 100 mL of anhydrous THF is added dropwise over 10 minutes to a solution of 0.1 mol of O-acetylthreonine methyl ester isocyanate and 0.35 mol pyridine in 100 mL THF at room temperature under N$_2$. The reaction mixture is stirred at room temperature for 2 hours. After 2 hours the solvent is removed by rotary evaporator. A solution of 0.11 mol hydroxylamine hydrochloride and 0.1 mol trimethyl orthoformate in CH$_3$OH is added, and the reaction mixture is heated to reflux under N$_2$ for 1 hour. The reaction mixture is reduced to about ¼ volume by rotary evaporator, and water is added. N-[4-(hydroxyiminomethyl)phenyl]-N'-(1-methoxycarbonyl-2-acetyloxypropyl)urea forms after several hours of stirring. The product is isolated by filtration and dried overnight in a vacuum oven at 50°–55° C.

EXAMPLE 19

0.35 mol diphosgene is added dropwise over 1 hour to a mixture of 0.28 mol of the methyl ester of S-acetylcysteine and 0.4 g activated charcoal in 400 mL dioxane under N$_2$. The reaction mixture is then heated and stirred at reflux for 2½ hours. The reaction mixture is then cooled, filtered, and concentrated to dryness by rotary evaporator, keeping exposure to moisture to a minimum. The crude product is re-dissolved in 100 mL THF, and the pH of the solution is adjusted to 5.5–6.0 by addition of pyridine. The product mixture is again filtered, and the filtrate fractionally distilled to give S-acetylcysteine methyl ester isocyanate.

A solution of 0.1 mol of 4-aminobenzaldehyde ethylene glycol acetal in 100 mL of anhydrous THF is added dropwise over 10 minutes to a solution of 0.1 mol of S-acetylcysteine methyl ester isocyanate and 0.35 mol pyridine in 100 mL THF at room temperature under N$_2$. The reaction mixture is stirred at room temperature for 2 hours. After 2 hours the solvent is removed by rotary evaporator. A solution of 0.11 mol hydroxylamine hydrochloride and 0.1 mol trimethyl orthoformate in CH$_3$OH is added, and the reaction mixture is heated to reflux under N$_2$ for 1 hour. The reaction mixture is reduced to about ¼ volume by rotary evaporator, and water is added. N-[4-(hydroxyiminomethyl)phenyl]-N'-[1-methoxycarbonyl-2-(acetylthio)ethyl]urea forms after several hours of stirring. The product is isolated by filtration and dried overnight in a vacuum oven at 50°–55° C.

EXAMPLE 20

0.35 mol diphosgene is added dropwise over 1 hour to a mixture of 0.28 mol of the methyl ester of O-acetyl-tyrosine and 0.4 g activated charcoal in 400 mL dioxane under N$_2$. The reaction mixture is then heated and stirred at reflux for 2½ hours. The reaction mixture is then cooled, filtered, and concentrated to dryness by rotary evaporator, keeping exposure to moisture to a minimum. The crude product is re-dissolved in 100 mL THF, and the pH of the solution is adjusted to 5.5–6.0 by addition of pyridine. The product mixture is again filtered, and the filtrate fractionally distilled to give O-acetyltyrosine methyl ester isocyanate.

A solution of 0.1 mol of 4-aminobenzaldehyde ethylene glycol acetal in 100 mL of anhydrous THF is added dropwise over 10 minutes to a solution of 0.1 mol of O-acetyltyrosine methyl ester isocyanate and 0.35 mol pyridine in 100 mL THF at room temperature under N$_2$. The reaction mixture is stirred at room temperature for 2 hours. After 2 hours the solvent is removed by rotary evaporator. A solution of 0.11 mol hydroxylamine hydrochloride and 0.1 mol trimethyl orthoformate in CH$_3$OH is added, and the reaction mixture is heated to reflux under N$_2$ for 1 hour. The reaction mixture is reduced to about ¼ volume by rotary evaporator, and water is added. N-[4-(hydroxyiminomethyl)phenyl]-N'-[1-methoxycarbonyl-2-(4-acetyloxyphenyl)ethyl]urea forms after several hours of stirring. The product is isolated by filtration and dried overnight in a vacuum oven at 50°–55° C.

EXAMPLE 21

0.35 mol diphosgene is added dropwise over 1 hour to a mixture of 0.28 mol of the methyl ester of asparagine and 0.4 g activated charcoal in 400 mL dioxane under N$_2$. The reaction mixture is then heated and stirred at reflux for 2½ hours. The reaction mixture is then cooled, filtered, and concentrated to dryness by rotary evaporator, keeping exposure to moisture to a minimum. The crude product is re-dissolved in 100 mL THF, and the pH of the solution is adjusted to 5.5–6.0 by addition of pyridine. The product mixture is again filtered, and the filtrate is fractionally distilled to give asparagine methyl ester isocyanate.

A solution of 0.1 mol of 4-aminobenzaldehyde ethylene glycol acetal in 100 mL of anhydrous THF is added dropwise over 10 minutes to a solution of 0.1 mol of asparagine methyl ester isocyanate and 0.35 mol pyridine in 100 mL THF at room temperature under N$_2$. The reaction mixture is stirred at room temperature for 2 hours. After 2 hours the solvent is removed by rotary evaporator. A solution of 0.11 mol hydroxylamine hydrochloride and 0.1 mol trimethyl orthoformate in CH$_3$OH is added, and the reaction mixture is heated to reflux under N$_2$ for 1 hour. The reaction mixture is reduced to about ¼ volume by rotary evaporator, and water is added. N-[4-(hyroxyiminomethyl)phenyl]-N'-(1-methoxycarbonyl-2-carbamoylethyl)urea forms after several hours of stirring. The product is isolated by filtration and dried overnight in a vacuum oven at 50°–55° C.

EXAMPLE 22

0.35 mol diphosgene is added dropwise over 1 hour to a mixture of 0.28 mol of the methyl ester of glutamine and 0.4 g activated charcoal in 400 mL dioxane under $N_2$. The reaction mixture is then heated and stirred at reflux for 2½ hours. The reaction mixture is then cooled, filtered, and concentrated to dryness by rotary evaporator, keeping exposure to moisture to a minimum. The crude product is re-dissolved in 100 mL THF, and the pH of the solution is adjusted to 5.5–6.0 by addition of pyridine. The product mixture is again filtered, and the filtrate is fractionally distilled to give glutamine methyl ester isocyanate.

A solution of 0.1 mol of 4-aminobenzaldehyde ethylene glycol acetal in 100 mL of anhydrous THF is added dropwise over 10 minutes to a solution of 0.1 mol of glutamine methyl ester isocyanate and 0.35 mol pyridine in 100 mL THF at room temperature under $N_2$. The reaction mixture is stirred at room temperature for 2 hours. After 2 hours the solvent is removed by rotary evaporator. A solution of 0.11 mol hydroxylamine hydrochloride and 0.1 mol trimethyl orthoformate in $CH_3OH$ is added, and the reaction mixture is heated to reflux under $N_2$ for 1 hour. The reaction mixture is reduced to about ¼ volume by rotary evaporator, and water is added. N-[4-(hydroxyiminomethyl)phenyl]-N'-(1-methoxycarbonyl-3-carbamoylpropyl)urea forms after several hours of stirring. The product is isolated by filtration and dried overnight in a vacuum oven at 50°–55° C.

EXAMPLE 23

0.35 mol diphosgene is added dropwise over 1 hour to a mixture of 0.28 mol of the methyl ester of ε-N-acetyllysine and 0.4 g activated charcoal in 400 mL dioxane under $N_2$. The reaction mixture is then heated and stirred at reflux for 2½ hours. The reaction mixture is then cooled, filtered, and concentrated to dryness by rotary evaporator, keeping exposure to moisture to a minimum. The crude product is re-dissolved in 100 mL THF, and the pH of the solution is adjusted to 5.5–6.0 by addition of pyridine. The product mixture is again filtered, and the filtrate product is fractionally distilled to give ε-N-acetyllysine methyl ester isocyanate.

A solution of 0.1 mol of 4-aminobenzaldehyde ethylene glycol acetal in 100 mL of anhydrous THF is added dropwise over 10 minutes to a solution of 0.1 mol of ε-N-acetyllysine methyl ester isocyanate and 0.35 mol pyridine in 100 mL THF at room temperature under $N_2$. The reaction mixture is stirred at room temperature for 2 hours. After 2 hours the solvent is removed by rotary evaporator. A solution of 0.11 mol hydroxylamine hydrochloride and 0.1 mol trimethyl orthoformate in $CH_3OH$ is added, and the reaction mixture is heated to reflux under $N_2$ for 1 hour. The reaction mixture is reduced to about ¼ volume by rotary evaporator, and water is added. N-[4-(hydroxyiminomethyl)phenyl]-N'-(1-methoxycarbonyl-5-acetamidopentyl)urea forms after several hours of stirring. The product is isolated by filtration and dried overnight in a vacuum oven at 50°–55° C.

EXAMPLE 24

0.35 mol diphosgene is added dropwise over 1 hour to a mixture of 0.28 mol of the methyl ester of 2-amino-3-(3-acetyl-5-imidazole)propanoic acid and 0.4 g activated charcoal in 400 mL dioxane under $N_2$. The reaction mixture is then heated and stirred at reflux for 2½ hours. The reaction mixture is then cooled, filtered, and concentrated to dryness by rotary evaporator, keeping exposure to moisture to a minimum. The crude product is re-dissolved in 100 mL THF, and the pH of the solution is adjusted to 5.5–6.0 by addition of pyridine. The product mixture is again filtered, and the filtrate is fractionally distilled to give 2-isocyanato-3-(3-acetyl-5-imidazole)propanoic acid methyl ester.

A solution of 0.1 mol of 4-aminobenzaldehyde ethylene glycol acetal in 100 mL of anhydrous THF is added dropwise over 10 minutes to a solution of 0.1 mol of 2-isocyanato-3-(3-acetyl-5-imidazole)propanoic acid methyl ester and 0.35 mol pyridine in 100 mL THF at room temperature under $N_2$. The reaction mixture is stirred at room temperature for 2 hours. After 2 hours the solvent is removed by rotary evaporator. A solution of 0.11 mol hydroxylamine hydrochloride and 0.1 mol trimethyl orthoformate in $CH_3OH$ is added, and the reaction mixture is heated to reflux under $N_2$ for 1 hour. The reaction mixture is reduced to about ¼ volume by rotary evaporator, and water is added. N-[4-(hydroxyiminomethyl)phenyl]-N'-[1-methoxycarbonyl-2-(3-acetyl-5-imidazolyl)ethyl]urea forms after several hours of stirring. The product is isolated by filtration and dried overnight in a vacuum oven at 50°–55° C.

EXAMPLE 25

N-[4-(1-hydroxyiminoethyl)phenyl]-N'-methoxycarbonylmethylurea is made as follows: A solution of 2.7 g 4-aminoacetophenone in 40 mL THF is added dropwise to a solution of 2.3 g glycine methyl ester isocyanate and 5 mL pyridine in 40 mL THF, and the reaction mixture is stirred for 3 hours. The solvent is then removed by rotary evaporator to leave an off-white solid. The solid is dispersed in 50 mL $CH_3OH$, and 1.53 g hydroxylamine hydrochloride and 6.4 g trimethyl orthoformate are added. The reaction mixture is heated to reflux for 1 hour. The solvent is removed by rotary evaporator to leave an orange oil. Addition of water to the oil results in formation of off-white crystals. The crystals are treated again with 1.0 g hydroxylamine hydrochloride and 3.0 g trimethyl orthoformate in 50 mL $CH_3OH$ at reflux for 1 hour. The product mixture is concentrated by rotary evaporator, water is added, and the solid which forms (mp. 179°–181° C.) is shown by NMR spectroscopy to be pure product, 2.55 g. $^{13}C$ NMR (acetone-$d_6$): δ172, —COO—; 156; —NCON—; 142, —C=N—; 118, 127, 131, 153, phenyl; 52, $CH_3O$—; 42, —$CH_2CO$—; 12, $CH_3C$=N—. $^1H$ NMR (acetone-$d_6$): δ10.1 s, 1H, —NOH; 8.4 s, 1H, φ—NH—CO—; 7.4–7.6 m, 4H, phenyl; 6.2 t, 1H, —$CH_2N\overline{H}\overline{C}O$—; 4.0 d, 2H, —$NHC\underline{H}_2$—; 3.7 s, 3H. —$OC\underline{H}_3$; 2.1 s, 3H, $C\underline{H}_3C$=N—.

EXAMPLE 26

A solution of 0.02 mol 4-aminoacetophenone in 40 mL THF is added dropwise to a solution of 0.02 mol of glycine ethyl ester isocyanate and 5 mL pyridine in 40 mL THF, and the reaction mixture is stirred for 3 hours. The solvent is then removed by rotary evaporator. The residue is dispersed in 50 mL $CH_3OH$, and 0.022 mol hydroxylamine hydrochloride and 0.06 mol trimethyl orthoformate are added. The reaction mixture is heated to reflux for 10 hours. The solvent is removed by rotary evaporator. Addition of water to the residue results in precipitation of N-[4-(1-hydroxyiminoethyl)phenyl]-N'- ethoxycarbonylmethylurea, which is isolated by filtration and dried.

EXAMPLE 27

A solution of 0.02 mol 4-aminoacetophenone in 40 mL THF is added dropwise to a solution of 0.02 mol of glycine n-propyl ester isocyanate and 5 mL pyridine in 40 mL THF, and the reaction mixture is stirred for 3 hours. The solvent is then removed by rotary evaporator. The residue is dispersed in 50 mL CH$_3$OH, and 0.022 mol hydroxylamine hydrochloride and 0.06 mol trimethyl orthoformate are added. The reaction mixture is heated to reflux for 10 hours. The solvent is removed by rotary evaporator. Addition of water to the residue results in precipitation of N-[4-(1-hydroxyiminoethyl)-phenyl]-N'-(n-propoxycarbonylmethyl)urea, which is isolated by filtration and dried.

EXAMPLE 28

A solution of 0.02 mol 4-aminoacetophenone in 40 mL THF is added dropwise to a solution of 0.02 mol of glycine isopropyl ester isocyanate and 5 mL pyridine in 40 mL THF, and the reaction mixture is stirred for 3 hours. The solvent is then removed by rotary evaporator. The residue is dispersed in 50 mL CH$_3$OH, and 0.022 mol hydroxylamine hydrochloride and 0.06 mol trimethyl orthoformate are added. The reaction mixture is heated to reflux for 10 hours. The solvent is removed by rotary evaporator. Addition of water to the residue results in precipitation of N-[4-(1-hydroxyiminoethyl)-phenyl]-N'-isopropoxycarbonylmethylurea, which is isolated by filtration and dried.

EXAMPLE 29

A solution of 0.02 mol 4-aminoacetophenone in 40 mL THF is added dropwise to a solution of 0.02 mol of glycine t-butyl ester isocyanate and 5 mL pyridine in 40 mL THF, and the reaction mixture is stirred for 3 hours. The solvent is then removed by rotary evaporator. The residue is dispersed in 50 mL CH$_3$OH, and 0.022 mol hydroxylamine hydrochloride and 0.06 mol trimethyl orthoformate are added. The reaction mixture is heated to reflux for 10 hours. The solvent is removed by rotary evaporator. Addition of water to the residue results in precipitation of N-[4-(1-hydroxyiminoethyl)phenyl]-N'-(t-butoxycarbonylmethyl)urea, which is isolated by filtration and dried.

EXAMPLE 30

A solution of 0.02 mol 4-aminoacetophenone in 40 mL THF is added dropwise to a solution of 0.02 mol of glycine phenyl ester isocyanate and 5 mL pyridine in 40 mL THF, and the reaction mixture is stirred for 3 hours. The solvent is then removed by rotary evaporator. The residue is dispersed in 50 mL CH$_3$OH, and 0.022 mol hydroxylamine hydrochloride and 0.06 mol trimethyl orthoformate are added. The reaction mixture is heated to reflux for 10 hours. The solvent is removed by rotary evaporator. Addition of water to the residue results in precipitation of crystals of N-[4-(1-hydroxyiminoethyl)-phenyl]-N'-phenoxycarbonylmethylurea, which is isolated by filtration and dried.

EXAMPLE 31

A solution of 2.7 g 4-aminoacetophenone in 40 mL THF is added dropwise to a solution of 0.02 mol of alanine methyl ester isocyanate and 5 mL pyridine in 40 mL THF, and the reaction mixture is stirred for 3 hours. The solvent is then removed by rotary evaporator. The residue is dispersed in 50 mL CH$_3$OH, and 0.022 mol hydroxylamine hydrochloride and 0.06 mol trimethyl orthoformate are added. The reaction mixture is heated to reflux for 10 hours. The solvent is removed by rotary evaporator. Addition of water to the residue results in precipitation of N-[4-(1-hydroxyiminoethyl)phenyl]-N'-(1-methoxycarbonylethyl)urea, which is isolated by filtration and dried.

EXAMPLE 32

A solution of 2.7 g 4-aminoacetophenone in 40 mL THF is added dropwise to a solution of 0.02 mol of valine methyl ester isocyanate and 5 mL pyridine in 40 mL THF, and the reaction mixture is stirred for 3 hours. The solvent is then removed by rotary evaporator. The residue is dispersed in 50 mL CH$_3$OH, and 0.022 mol hydroxylamine hydrochloride and 0.06 g trimethyl orthoformate are added. The reaction mixture is heated to reflux for 10 hours. The solvent is removed by rotary evaporator. Addition of water to the residue results in precipitation of N-[4-(1-hydroxyiminoethyl)phenyl]-N'-(1-methoxycarbonyl-2-methylpropyl)urea, which is isolated by filtration and dried.

EXAMPLE 33

A solution of 2.7 g 4-aminoacetophenone in 40 mL THF is added dropwise to a solution of 0.02 mol of leucine methyl ester isocyanate and 5 mL pyridine in 40 mL THF, and the reaction mixture is stirred for 3 hours. The solvent is then removed by rotary evaporator. The residue is dispersed in 50 mL CH$_3$OH, and 0.022 mol hydroxylamine hydrochloride and 0.06 mol trimethyl orthoformate are added. The reaction mixture is heated to reflux for 10 hours. The solvent is removed by rotary evaporator. Addition of water to the residue results in precipitation of N-[4-(1-hydroxyiminoethyl)phenyl]-N'-(1-methoxycarbonyl-3-methylbutyl)urea, which is isolated by filtration and dried.

EXAMPLE 34

A solution of 2.7 g 4-aminoacetophenone in 40 mL THF is added dropwise to a solution of 0.02 mol of isoleucine methyl ester isocyanate and 5 mL pyridine in 40 mL THF, and the reaction mixture is stirred for 3 hours. The solvent is then removed by rotary evaporator. The residue is dispersed in 50 mL CH$_3$OH, and 0.022 mol hydroxylamine hydrochloride and 0.06 mol trimethyl orthoformate are added. The reaction mixture is heated to reflux for 10 hours. The solvent is removed by rotary evaporator. Addition of water to the residue results in precipitation of N-[4-(1-hydroxyiminoethyl)-phenyl]-N'-(1-methoxycarbonyl-2-methylbutyl)urea, which is isolated by filtration and dried.

EXAMPLE 35

A solution of 2.7 g 4-aminoacetophenone in 40 mL THF is added dropwise to a solution of 0.02 mol of phenylalanine methyl ester isocyanate and 5 mL pyridine in 40 mL THF, and the reaction mixture is stirred for 3 hours. The solvent is then removed by rotary evaporator. The residue is dispersed in 50 mL CH$_3$OH, and 0.022 mol hydroxylamine hydrochloride and 0.06 mol trimethyl orthoformate are added. The reaction mixture is heated to reflux for 10 hours. The solvent is removed by rotary evaporator. Addition of water to the residue results in precipitation of N-[4-(1-hydroxyiminoethyl)phenyl]-N'-(1-methoxycarbonyl-2-

EXAMPLE 36

A solution of 2.7 g 4-aminoacetophenone in 40 mL THF is added dropwise to a solution of 0.02 mol of 2-isocyanato-3-(1-acetyl-3-indole)propanoic acid methyl ester and 5 mL pyridine in 40 mL THF, and the reaction mixture is stirred for 3 hours. The solvent is then removed by rotary evaporator. The residue is dispersed in 50 mL CH$_3$OH, and 0.022 mol hydroxylamine hydrochloride and 0.06 mol trimethyl orthoformate are added. The reaction mixture is heated to reflux for 10 hours. The solvent is removed by rotary evaporator. Addition of water to the residue results in precipitation of N-[4-(1-hydroxyiminoethyl)phenyl]-N'-[1-methoxycarbonyl-2-(1-acetyl-3-indolyl)ethyl]urea, which is isolated by filtration and dried.

EXAMPLE 37

A solution of 2.7 g 4-aminoacetophenone in 40 mL THF is added dropwise to a solution of 0.02 mol of methionine methyl ester isocyanate and 5 mL pyridine in 40 mL THF, and the reaction mixture is stirred for 3 hours. The solvent is then removed by rotary evaporator. The residue is dispersed in 50 mL CH$_3$OH, and 0.022 mol hydroxylamine hydrochloride and 0.06 mol trimethyl orthoformate are added. The reaction mixture is heated to reflux for 10 hours. The solvent is removed by rotary evaporator. Addition of water to the residue results in precipitation of N-[4-(1-hydroxyiminoethyl)phenyl]-N'-(1-methoxycarabonyl-3-methylthiopropyl)urea, which is isolated by filtration and dried.

EXAMPLE 38

A solution of 2.7 g 4-aminoacetophenone in 40 mL THF is added dropwise to a solution of 0.02 mol of O-acetylserine methyl ester isocyanate and 5 mL pyridine in 40 mL THF, and the reaction mixture is stirred for 3 hours. The solvent is then removed by rotary evaporator. The residue is dispersed in 50 mL CH$_3$OH, and 0.022 mol hydroxylamine hydrochloride and 0.06 mol trimethyl orthoformate are added. The reaction mixture is heated to reflux for 10 hours. The solvent is removed by rotary evaporator. Addition of water to the residue results in precipitation of N-[4-(1-hydroxyiminoethyl)phenyl]-N'-(1-methoxycarbonyl-2-acetyloxyethyl)urea, which is isolated by filtration and dried.

EXAMPLE 39

A solution of 2.7 g 4-aminoacetophenone in 40 mL THF is added dropwise to a solution of 0.02 mol of O-acetylthreonine methyl ester isocyanate and 5 mL pyridine in 40 mL THF, and the reaction mixture is stirred for 3 hours. The solvent is then removed by rotary evaporator. The residue is dispersed in 50 mL CH$_3$OH, and 0.222 mol hydroxylamine hydrochloride and 0.06 mol trimethyl orthoformate are added. The reaction mixture is heated to reflux for 10 hours. The solvent is removed by rotary evaporator. Addition of water to the residue results in precipitation of N-[4-(1-hydroxyiminoethyl)phenyl]-N'-(1-methoxycarbonyl-2-acetyloxypropyl)urea, which is isolated by filtration and dried.

EXAMPLE 40

A solution of 2.7 g 4-aminoacetophenone in 40 mL THF is added dropwise to a solution of 0.02 mol of S-acetylcysteine methyl ester isocyanate and 5 mL pyridine in 40 mL THF, and the reaction mixture is stirred for 3 hours. The solvent is then removed by rotary evaporator. The residue is dispersed in 50 mL CH$_3$OH, and 0.022 mol hydroxylamine hydrochloride and 0.06 mol trimethyl orthoformate are added. The reaction mixture is heated to reflux for 10 hours. The solvent is removed by rotary evaporator. Addition of water to the residue results in precipitation of N-[4-(1-hydroxyiminoethyl)phenyl]-N'-[1-methoxycarbonyl-2-(acetylthio)ethyl]urea, which is isolated by filtration and dried.

EXAMPLE 41

A solution of 2.7 g 4-aminoacetophenone in 40 mL is THF is dropwise to a solution of 0.02 mol of O-acetyltyrosine methyl ester isocyanate and 5 mL pyridine in 40 mL THF, and the reaction mixture is stirred for 3 hours. The solvent is then removed by rotary evaporator. The residue is dispersed in 50 mL CH$_3$OH, and 0.022 mol hydroxylamine hydrochloride and 0.06 mol trimethyl orthoformate are added. The reaction mixture is heated to reflux for 10 hours. The solvent is removed by rotary evaporator. Addition of water to the residue results in precipitation of N-[4-(1-hydroxyiminoethyl)phenyl]-N'-[1-methoxycarbonyl-2-(4-acetyloxyphenyl)ethyl]urea, which is isolated by filtration and dried.

EXAMPLE 42

A solution of 2.7 g 4-aminoacetophenone in 40 mL is THF added dropwise to a solution of 0.02 mol of asparagine methyl ester isocyanate and 5 mL pyridine in 40 mL THF, and the reaction mixture is stirred for 3 hours. The solvent is then removed by rotary evaporator. The residue is dispersed in 50 mL CH$_3$OH, and 0.022 mol hydroxylamine hydrochloride and 0.06 mol trimethyl orthoformate are added. The reaction mixture is heated to reflux for 10 hours. The solvent is removed by rotary evaporator. Addition of water to the residue results in precipitation of N-[4-(1-hydroxyiminoethyl)phenyl]-N'-(1-methoxycarbonyl-2-carbamoylethyl)urea, which is isolated by filtration and dried.

EXAMPLE 43

A solution of 2.7 g 4-aminoacetophenone in 40 mL THF is added dropwise to a solution of 0.02 mol of glutamine methyl ester isocyanate and 5 mL pyridine in 40 mL THF, and the reaction mixture is stirred for 3 hours. The solvent is then removed by rotary evaporator. The residue is dispersed in 50 mL CH$_3$OH, and 0.022 mol hydroxylamine hydrochloride and 0.06 mol trimethyl orthoformate are added. The reaction mixture is heated to reflux for 10 hours. The solvent is removed by rotary evaporator. Addition of water to the residue results in precipitation of N-[4-(1-hydroxyiminoethyl)phenyl]-N'-(1-methoxycarbonyl-3-carbamoylpropyl)urea, which is isolated by filtration and dried.

EXAMPLE 44

A solution of 0.02 mol 4-aminoacetophenone in 40 mL THF is added dropwise to a solution of 0.02 mol dimethyl aspartate isocyanate and 5 mL pyridine in 40 mL THF, and the reaction mixture is stirred for 3 hours. The solvent is then removed by rotary evaporator. The residue is dispersed in 50 mL CH$_3$OH, and 0.022 mol hydroxylamine hydrochloride and 0.06 mol trimethyl orthoformate are added. The reaction mixture is heated to reflux for 10 hours. The solvent is removed by rotary evaporator. Addition of water to the residue results in precipitation of N-[4-(1-hydroxyiminoethyl)phenyl]-N'-[1,2-bis(methoxycarbonyl)ethyl]urea, which is isolated by filtration and dried.

EXAMPLE 45

A solution of 0.02 mol 4-aminoacetophenone in 40 mL THF is added dropwise to a solution of 0.02 mol dimethyl glutamate isocyanate and 5 mL pyridine in 40 mL THF, and the reaction mixture is stirred for 3 hours. The solvent is then removed by rotary evaporator. The residue is dispersed in 50 mL CH₃OH, and 0.022 mol hydroxylamine hydrochloride and 0.06 mol trimethyl orthoformate is added. The reaction mixture is heated to reflux for 10 hours. The solvent is removed by rotary evaporator. Addition of water to the residue results in precipitation of N-[4-(1-hydroxyiminoethyl)phenyl]-N'-[1,3-bis(methoxycarbonyl)propyl]urea, which is isolated by filtration and dried.

EXAMPLE 46

A solution of 0.02 mol 4-aminoacetophenone in 40 mL THF is added dropwise to a solution of 0.02 mol ε-N-acetyllysine methyl ester isocyanate and 5 mL pyridine in 40 mL, and the reactor mixture is stirred for 3 hours. The solvent is then removed by rotary evaporator. The residue is dispersed in 50 mL CH₃OH, and 0.022 mol hydroxylamine hydrochloride and 0.06 mol trimethyl orthoformate are added. The reaction mixture is refluxed for 10 hours. The solvent is removed by rotary evaporator. Addition of water to the residue results in precipitation of N-[4-(1-hydroxyiminoethyl)phenyl]-N'-(1-methoxycarbonyl-5-acetamidopropyl)urea, which is isolated by filtration and dried.

EXAMPLE 47

A solution of 0.02 mol 2.7 g 4-aminoacetophenone in 40 mL THF is added dropwise to a solution of 0.02 mol 2-isocyanato-3-(3-acetyl-5-imidazole)propanoic acid methyl ester and 5 mL pyridine in 40 mL THF, and the reaction mixture is stirred for 3 hours. The solvent is then removed by rotary evaporator. The residue is dispersed in 50 mL CH₃OH, and 0.022 mol hydroxylamine hydrochloride and 0.06 mol trimethyl orthoformate are added. The reaction mixture is heated to reflux for 10 hours. The solvent is removed by rotary evaporator. Addition of water to the residue results in precipitation of N-[4-(1-hydroxyiminoethyl)phenyl]-N'-[1-methoxycarbonyl-2-(3-acetyl-5-imidazolyl)ethyl]urea, which is isolated by filtration and dried.

EXAMPLE 48

A solution of 0.02 mol 4-aminoacetophenone in 40 mL THF is added dropwise to a solution of 0.02 mol of dimethyl isocyanatomalonate and 5 mL pyridine in 40 mL THF, and the reaction mixture is stirred for 3 hours. The solvent is then removed by rotary evaporator. The residue is dispersed in 50 mL CH₃OH, and 0.022 mol hydroxylamine hydrochloride and 0.06 mol trimethyl orthoformate are added. The reaction mixture is heated to reflux for 10 hours. The solvent is removed by rotary evaporator. Addition of water to the residue results in precipitation of N-[4-(1-hydroxyiminoethyl)phenyl]-N'-bis(methoxycarbonyl)methylurea, which is isolated by filtration and dried.

As will be evident to those skilled in the art, various modifications of this invention can be made or followed in the light of the foregoing disclosure and discussion without departing from the spirit and scope of the disclosure or from the scope of the claims.

We claim:

1. A method of making a compound,

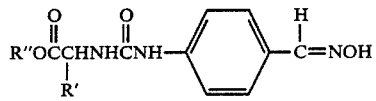

where R' contains no ethylenic or acetylenic unsaturation, has zero to 10 C atoms and is selected from (1) H, (2) hydrocarbyl, and (3) hydrocarbyl substituted with hydrocarbylcarbonylamino, di(hydrocarbylcarbonyl)amino, hydrocarbylcarbonyl(hydrocarbyl)amino, formylamino, diformylamino, formyl(hydrocarbyl)amino, hydrocarbyloxy, hydrocarbylthio, formylthio, hydrocarbylcarbonylthio, hydrocarbyloxycarbonyl, hydrocarbyl carboxyl, hydrocarbylamino, dihydrocarbylamino, formyl, 3-indolyl, 3-(1-hydrocarbyl)indolyl, 3-(1-hydrocarbylcarbonyl)indolyl, 3-(1-formyl)indolyl, carbamoyl, hydrocarbylcarbamoyl, dihydrocarbylcarbamoyl, 5-imidazolyl, 5-(3-hydrocarbyl)imidazolyl, 5-(3-hydrocarbylcarbonyl)imidazolyl, or 5-(3-formyl)imidazolyl; and where R" is phenyl or a C₁ to C₆ alkyl group, which comprises reacting a compound,

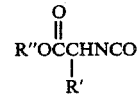

with an acetal of p-aminobenzaldehyde derived from a C₁ to C₆ monoalkanol or a C₁ to C₆ alkanediol and in the presence of pyridine, and then reacting the product of such reaction with hydroxylamine hydrochloride in an alcohol solvent.

2. A compound of the formula,

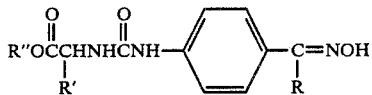

where each of R and R' have zero to 10 C atoms; R is H or hydrocarbyl; R' is (1) H, (2) hydrocarbyl, or (3) hydrocarbyl substituted with hydrocarbylcarbonylamino, di(hydrocarbylcarbonyl)amino, hydrocarbylcarbonyl(hydrocarbyl)amino, formylamino, diformylamino, formyl(hydrocarbyl)amino, hydrocarbyloxy, hydrocarbylthio, formylthio, hydrocarbylcarbonylthio, hydrocarbyloxycarbonyl, hydrocarbyl carboxyl, hydrocarbylamino, dihydrocarbylamino, formyl, 3-indolyl, 3-(1-hydrocarbyl)indolyl, 3-(1-hydrocarbylcarbonyl)indolyl, 3-(1-formyl)indolyl, carbamoyl, hydrocarbylcarbamoyl, dihydrocarbylcarbamoyl, 5-imidazolyl, 5-(3-hydrocarbyl)imidazolyl, 5-(3-hydrocarbylcarbonyl)imidazolyl, or 5-(3-formyl)imidazolyl; and where R" is phenyl or a C₁ to C₆ alkyl group.

3. A compound of the formula,

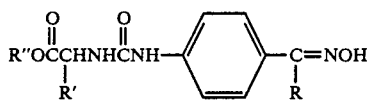

where each of R and R' have zero to 6 C atoms; R is H or hydrocarbyl; R' is (1) H, (2) hydrocarbyl, or (3) hydrocarbyl substituted with hydrocarbylcarbonylamino, di(hydrocarbylcarbonyl)amino, hydrocarbylcarbonyl(hydrocarbyl)amino, formylamino, diformylamino, formyl(hydrocarbyl)amino, hydrocarbyloxy, hydrocarbylthio, formylthio, hydrocarbylcarbonylthio, hydrocarbyloxycarbonyl, hydrocarbyl carboxyl, hydrocarbylamino, dihydrocarbylamino, formyl, 3-indolyl, 3-(1-hydrocarbyl)indolyl, 3-(1-hydrocarbylcarbonyl)indolyl, 3-(1-formyl)indolyl, carbamoyl, hydrocarbylcarbamoyl, dihydrocarbylcarbamoyl, 5-imidazolyl, 5-(3-hydrocarbyl)imidazolyl, 5-(3-hydrocarbylcarbonyl)imidazolyl, or 5-(3-formyl)imidazolyl; and where R" is phenyl or a $C_1$ to $C_6$ alkyl group.

4. N-[4-(1-hydroxyiminoethyl)phenyl]-N'-methoxycarbonylmethylurea.

5. N-[4-(hydroxyiminomethyl)phenyl]-N'-bis(methoxycarbonyl)methylurea.

6. N-[4-(hydroxyiminomethyl)phenyl]-N'-methoxycarbonylmethylurea.

7. N-[4-(hydroxyiminomethyl)phenyl]-N'-1-(methoxycarbonyl)ethylurea.

* * * * *